United States Patent [19]
Cohen-Bacrie et al.

[11] Patent Number: 6,135,957
[45] Date of Patent: Oct. 24, 2000

[54] METHOD OF AND APPARATUS FOR ECHOGRAPHIC DETERMINATION OF THE VISCOSITY AND THE PRESSURE GRADIENT IN A BLOOD VESSEL

[75] Inventors: Claude Cohen-Bacrie, Limeil-Brevannes; Fabrice Bruni, Combs-la-Ville; Odile Bonnefous, Nogent/Marne, all of France

[73] Assignee: U.S. Philips Corporation, New York, N.Y.

[21] Appl. No.: 09/236,238

[22] Filed: Jan. 22, 1999

[30] Foreign Application Priority Data

Jan. 23, 1998 [EP] European Pat. Off. .............. 98400145
Jul. 7, 1998 [FR] France ................................... 98 08695

[51] Int. Cl.$^7$ ....................................................... A61B 8/06
[52] U.S. Cl. ............................................ 600/438; 600/370
[58] Field of Search .................................... 600/368, 370, 600/438, 454–456

[56] References Cited

U.S. PATENT DOCUMENTS 4,646,754  3/1987  Seale .......................................... 73/575
5,411,028  5/1995  Bonnefous ............................... 600/438
5,535,747  7/1996  Katakura ................................. 600/438

FOREIGN PATENT DOCUMENTS

0225667B1  6/1987  European Pat. Off. .......... A61B 8/06
0430374B1  6/1991  European Pat. Off. .......... A61B 8/06
0603967A1  6/1994  European Pat. Off. .
9512822A1  5/1995  WIPO .

Primary Examiner—Francis J. Jaworski
Attorney, Agent, or Firm—Dwight H. Renfrew

[57] ABSTRACT

This invention includes a method of determining the viscosity and the pressure gradient in a blood vessel, including the acquisition of $n \geq 2$ blood speed values, corresponding to the same number of n radii of the blood vessel, determined along a diameter situated in a given axial position, formation of a blood speed vector by means of said n blood speed values, and evaluation of said viscosity and pressure gradient on the basis of a transformation of said blood speed value, including formation of a linear relation which directly links a flow rate vector (y) to the speed derivative vector (h), factorized by the viscosity ($\mu$), and to the pressure gradient vector ($\sigma$), and simultaneous evaluation of the two values to be determined for the viscosity ($\mu$) and the pressure gradient ($\sigma$) on the basis of said direct equation. The velocities are advantageously determined by correlation of ultrasonic signals supplied by an echography apparatus. This invention also includes apparatus for the practice of this method.

11 Claims, 4 Drawing Sheets

METHOD OF AND APPARATUS FOR ECHOGRAPHIC DETERMINATION OF THE VISCOSITY AND THE PRESSURE GRADIENT IN A BLOOD VESSEL

All references cited herein, as well as the priority documents European Patent Application 98400145.3 filed Jan. 23, 1998 and French Patent Application 9808695 filed Jul. 7, 1998, are incorporated herein by reference in their entirety and for all purposes to the same extent as if each individual publication or patent or patent application was specifically and individually indicated to be incorporated by reference in its entirety for all purposes.

FIELD OF THE INVENTION

The invention relates to a method of determining the viscosity and the pressure gradient in a blood vessel. The invention is used in the field of manufacture of ultrasonic echography apparatus, also referred to as echographs, for medical diagnosis.

BACKGROUND OF THE INVENTION

When in the medical field a patient has a cerebral or cardiac vascular injury, it is necessary to check the viscosity of the blood because this parameter plays an important role in the diagnosis of the vascular injury and in the determination of an appropriate treatment, for example a treatment on the basis of blood thinning medication. In order to determine the viscosity of the blood at present it is necessary to perform measurements on blood samples taken from the patient. This procedure has significant drawbacks. The result of the measurements is not immediately available and the taking of the blood samples itself is invasive and hence potentially contaminating. It is a further drawback that the taking of the blood samples must be periodically repeated so as to check the effect of the treatment; this could damage the vessels of the patient. No alternative for this method of determining the viscosity of blood is known at present. An invasive means is to be understood to mean herein the taking of a blood sample which necessitates, for example the introduction of a needle into the blood vessel so as to fill a syringe with a blood sample.

Patent EP 0 430 374 (U.S. Pat. No. 5,103,826, Bonnefous, Apr. 14, 1992) already discloses an ultrasonic echography apparatus which is provided with a system for the processing of ultrasonic signals in order to determine speed profiles of the blood in an artery. The echography apparatus includes a transducer which emits and receives ultrasonic signals from the region of an artery of a patient, and a transmitter stage which is connected to the probe. The processing system estimates the speed of the blood in the artery as a function of time and scanning depth while utilizing a method for the correlation of successive signals returned by the transducer.

SUMMARY OF THE INVENTION

It is an object of the invention to provide a method which can be carried out, without using invasive means, to determine the viscosity of the blood flowing in an artery under the influence of the cardiac pulsation which creates a pressure gradient, said operation being performed with a precision equal to or higher than that achieved by means of the known method which includes the analysis of samples taken.

This object is achieved by means of a method including the steps of: acquisition of a plurality of $n \geq 2$ values of the velocity of the blood speeds, in correspondence with an equal number of n radii of the blood vessel, determined along a diameter situated in a given axial position, and at different instants, formation of a vector of the blood speeds by means of said plurality of values of the blood speeds, and evaluation of said viscosity and the pressure gradient on the basis of a transformation of said vector of the blood speeds.

This method offers significant advantages because of the fact that it is as exact as the method utilizing samples, that it is faster and simpler to carry out, and that it can be repeated a large number of times without damaging the blood vessels of the patient because it is not invasive. Another important advantage resides in the fact that all problems concerning contamination of the patient or the laboratory staff are avoided since no blood sample whatsoever is taken or treated.

An ultrasonic echography apparatus is provided with means for carrying out the above method. The provided echography apparatus for the measurement and display of physiological parameters of the blood flowing in a blood vessel, comprises means for measuring the viscosity and the pressure gradient of the blood, which means include: means (200) for the acquisition of temporal signals supplied by an ultrasonic transducer (100) scanning a blood vessel along an echographic excitation axis (Z), means (300) for the processing of the temporal signals in the temporal domain so as to supply temporally correlated signals and a speed profile discretized in the direction of the excitation axis (Z), means (400) for: the estimation of a blood speed vector on the basis of a number of $n \geq 2$ speed values selected on the speed profile at different scanning depths (r) on the excitation axis (Z) in the blood vessel, and the evaluation of the viscosity of the blood ($\mu$) and the pressure gradient ($\sigma$) by transformation of said speed vector while utilizing a method as disclosed and claimed herein.

BRIEF DESCRIPTION OF THE DRAWINGS

The method will be described in detail hereinafter with reference to the accompanying diagrammatic drawings; therein.

DESCRIPTION OF THE PREFERRED EMBODIMENTS

The invention relates to an ultrasonic echography apparatus provided with an ultrasonic signal processing system for the determination of physiological parameters of the blood flowing in an artery which is examined in vivo in a tissue region, notably for the real time determination of the viscosity of the blood in a non-invasive manner, and for the determination of the blood pressure gradient in said artery.

Figure 1:
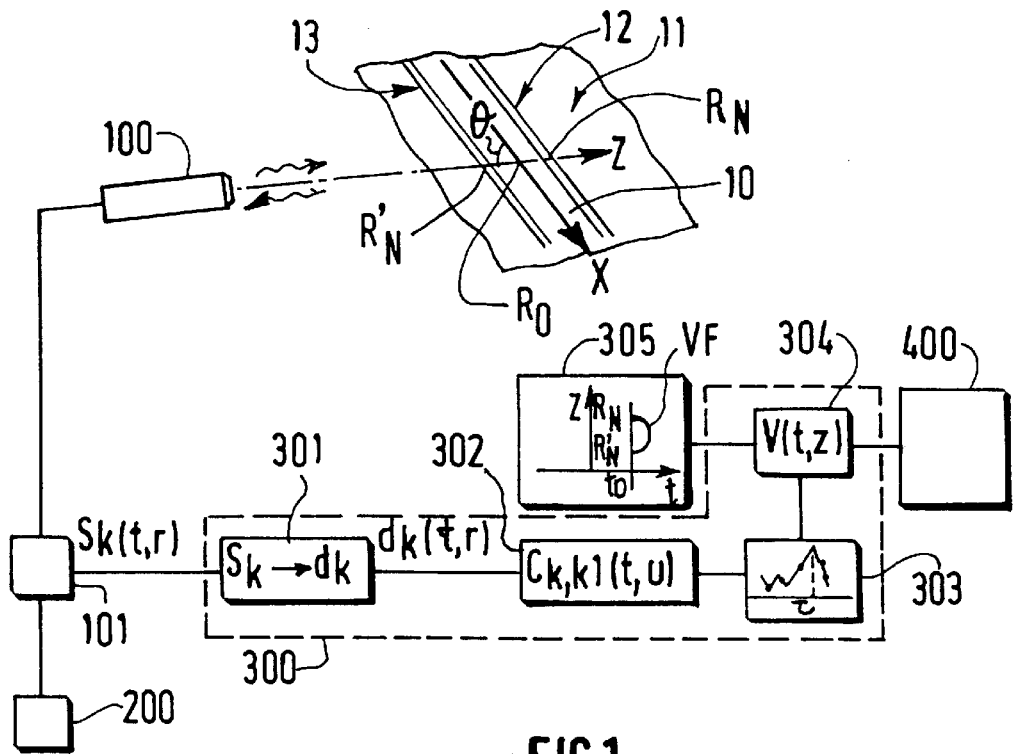
FIG. 1 shows a flow chart in the form of functional blocks illustrating the execution of the steps of the method of determining the viscosity of the blood in an artery and the pressure gradient due to the cardiac pulsation.
Figure 2A:
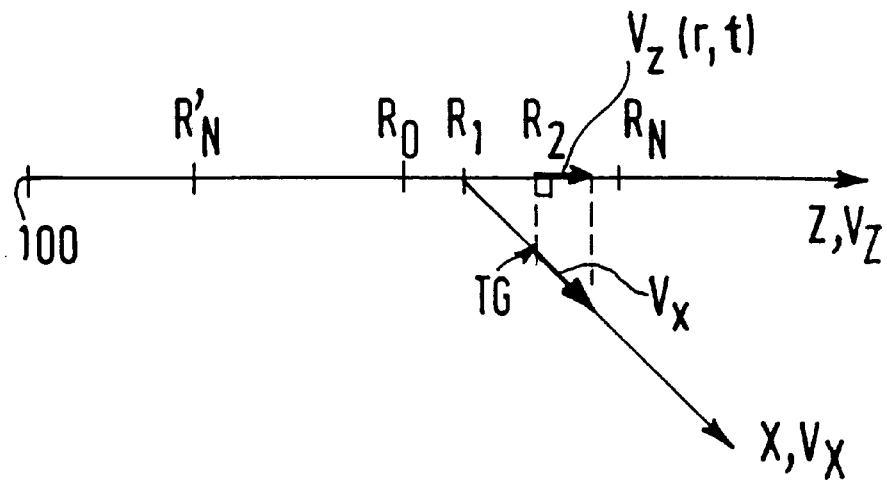
FIG. 2A shows an echographic scanning axis (Z) with respect to the longitudinal axis (X) of a blood vessel.

Referring to the FIGS. 1 and 2A, B and C, the apparatus includes at least one ultrasonic transducer 100 which is connected to a transmitter stage 200 and to a digital processing stage 300. The transducer 100 is applied to the tissue region 11 in order to examine the artery 10 having walls 12, 13. The beam emitted by the ultrasonic transducer is preferably a wide-band beam.

The transmitter stage 200 includes a sequencer which consists of an oscillator and a frequency divider which controls, with a recurrent period T, a generator whose electric excitation signals are applied to the transducer 100 which converts these signals into ultrasonic temporal signals which are emitted along an excitation axis Z with the recurrent period T. Each ultrasonic temporal signal in this emission system has a rank relating to the emission in time which is denoted as k, k+1, ..., with a period T. The transmitter stage 200, connected to the transducer 100, thus ensures the formation of an ultrasonic beam 50 for scanning the tissue region 11 containing the artery 10. During this examination, it is assumed that the blood flow takes place in the direction of the longitudinal axis X of the artery 10 and that the excitation axis Z of the ultrasonic beam from the transducer 100 encloses an angle $\Theta$ relative to the axis X. The scanning depths are discretized on the excitation axis Z, at points $R_0, R_1 \ldots R_n$ which are marked from a point 0, having the spatial co-ordinate $r_0$ on Z and situated at the intersection of the axis X and Z within the artery, to a point $R_N$ which has the spatial co-ordinate $r_N$ on Z and is situated on a wall, for example the wall 12 of the artery 10.

Referring to FIG. 1, a separating stage 101 is inserted between the stages 200, 300 and the transducer 100 in order to avoid overloading of the stages 200 and 300 by the transmitted signals. The processing stage 300 comprises, connected to the output of the separating stage 101, a high-frequency amplifier which incorporates gain compensation as a function of the scanning depth in the tissual region examined. The processing stage also comprises a fixed echo eliminator 301 which delivers, on the basis of a signal $S_k(t,r)$ from the separating stage 101, a temporal echographic signal $d_k(r,t)$ wherefrom fixed components which are due notably to the specular reflections from the walls 12, 13 of the artery 10 examined have been removed.

The signal $d_k(r,t)$ supplied by the fixed echo eliminator 301 is preferably processed in conformity with a correlation method as described in the patent EP 0 225 667 (U.S. Pat. No. 4,803,390, Bonnefous). This method will be described in brief hereinafter.

Figure 3A:
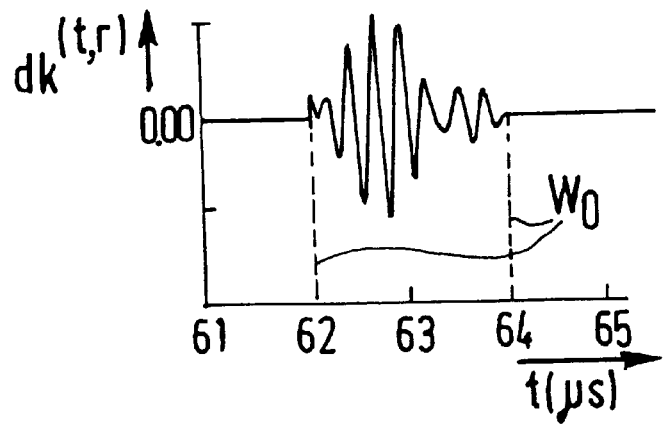
FIGS. 3A and 3B illustrate the first and second temporal signals.
Figure 3B:
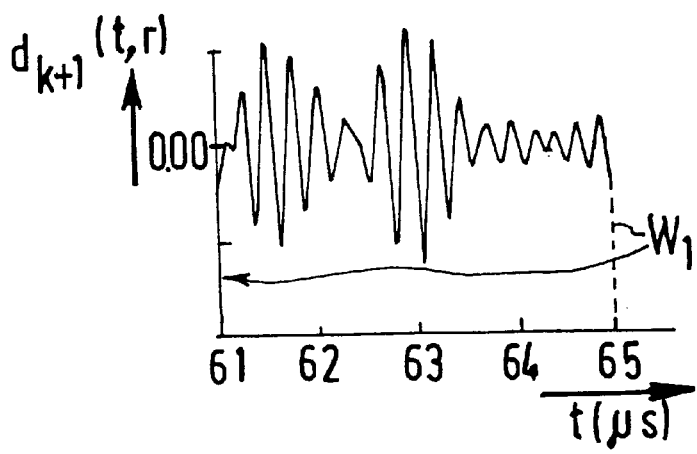
Figure 3C:
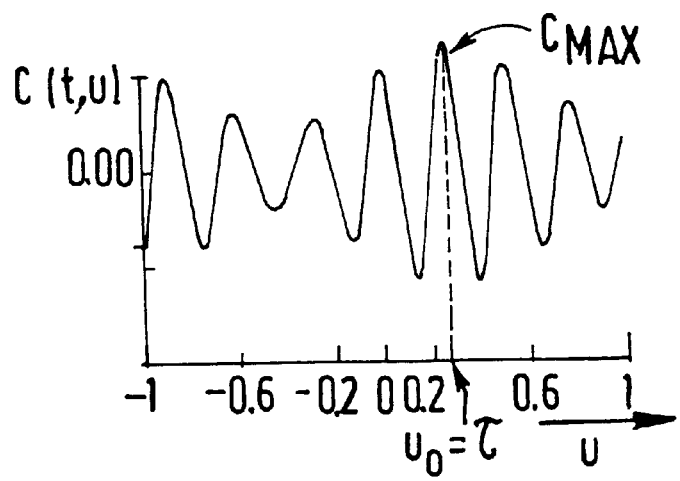
FIG. 3C illustrates a correlation signal.

According to this method, the processing system 300 determines the flow speed of blood structures, for example clusters of red corpuscles, called targets TG, at the instant t at which these targets coincide with the excitation axis Z and at discretized points on the excitation axis Z relating to the interior of the artery. It suffices to estimate the speeds between the center 0 and the point $R_N$ on the wall 12, because the speeds between the center 0 and the point $R'_N$ at the intersection of the axis Z and the other wall 13 of the artery are supposed to be symmetrical. The scanning depths along the axis Z are given by spatial co-ordinates r. The time in which an echo is returned by a target situated at a depth r is called t. The processing system 300 notably processes the temporal echographic signals of rank k which are called $d_k(r,t)$ and are formed by the intensities of the echoes returned by the targets at each discretized point on the axis Z at a depth from $r_0$ to $r_N$ in the artery 10, and produces the flow speed of the blood at these points. FIGS. 3A and 3B show such echographic temporal signals $d_k(r,t)$ and $d_{k+1}(r,t)$ with the intensity of the echographic signal in an arbitrary unit on the ordinate and on the abscissa temporal co-ordinates t in microseconds which correspond to the spatial co-ordinates r along the excitation axis Z.

Figure 2B:
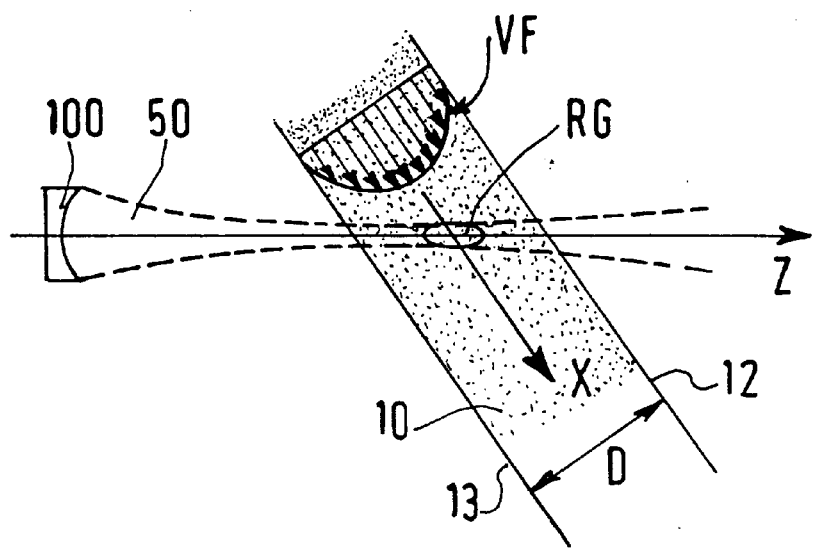
FIG. 2B illustrates the temporal shift between two echographic excitations.
Figure 2C:
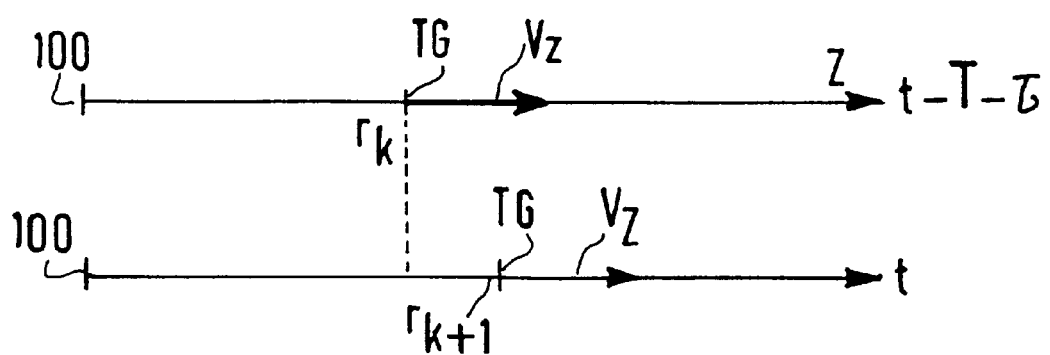
FIG. 2C illustrates a resolution window.

FIGS. 2A and 2B show that the echography apparatus is not sensitive to speeds other than those relating to the excitation axis Z. Therefore, neither the distances actually traveled along the axis X by the targets TG nor the speeds of these targets along the axis X are measured, but only their projections on the axis Z. The speed of a target is thus measured by way of its component $V_z(r,t)$ along the axis Z as a function of time t and the scanning depth r. In FIG. 2C the references $r_k$ and $r_{k+1}$ denote the depths of a target TG returning echoes in the signals of rank k and k+1, respectively. The component along the longitudinal axis X is deduced from $V_z(r,t)$ by the relation:

$$V_x(r,t) = V_z(r,t)/\cos \Theta \quad (1)$$

The processing system 300 executes a technique for correlating two successive echographic temporal signals of rank k and k+1. Referring to FIG. 2C, for this correlation technique it is necessary that a high percentage of the targets present in the ultrasonic beam during a first excitation of rank k remains present in the echographic beam during a later excitation of rank k+1, so that the correlation between the two successive temporal signals is sufficiently firm. Therefore, referring to FIG. 2B, the correlation is performed within a given resolution window or range gate RG which has a dimension w chosen so that this requirement is readily satisfied. For example, if the blood has a flow speed of the order of 1 m/s and if the period T between two excitations equals 100 $\mu$s, corresponding to an excitation frequency of the order of 10 kHz, the displacement of the targets between two successive excitations will be of the order of 0.1 mm. This displacement is quite small in comparison with the dimensions of a suitably chosen range gate RG of the order of 1 mm along the axis X and 0.3 mm along the axis Z. In that case approximately 20% of the targets leave the range gate during the period T; approximately 20% enter this range gate and a high percentage of targets remains present therein.

The basic idea of the processing carried out by the system 300 in order to determine the speed at a discretized point on the axis Z is that an ultrasonic temporal signal $d_{k+1}(r,t)$, returned by a target in motion, situated within the range gate RG' has been emitted by an echographic excitation of rank k+1 along Z, at the instant t and is the replica of a previous temporal signal emitted by an echographic excitation of rank k along the same axis Z at the instant t-T, returned by the same target at the instant t-T-$\tau$, where $\tau$ is the supplementary time or time shift incurred by the later temporal signal, due to the displacement of the target during the interval T, while travelling the path probe-target-probe.

Thus, in the first place two successive echographic temporal signals returned by the same target are linked by the relation:

$$d_{k+1}(t) = d_k(t-T-\tau) \qquad (2)$$

Therefore, the temporal shift $\tau$ is given by:

$$\tau = 2V_z(r,t)/c \qquad (3)$$

where c is the speed of sound in vacuum and by extension in the tissues. The formula (3) enables determination of the components $V_z(r,t)$ of the speeds of the targets at each discrete point having spatial co-ordinates r by making an approximation on the basis of the fact that the axial speed $V_z(r,t)$ is very low in relation to the speed of sound c, and that the displacement of a target is very small in relation to the distance from the transducer to the target during a period T.

Consequently, the flow speed can be measured by means of an echography apparatus provided with a processing system 300 which includes means for measuring the time shift $\tau$ induced by the targets between two echographic excitations.

By first order approximation, the intercorrelation function between the two successive temporal signals is formed as:

$$C_{k,k+1}(t_0, u) = \int_0^{t_0+w_0} d_k(t) d_{k+1}(t+u) dt \qquad (4)$$

in which the time $t_0$ is linked to the scanning depth r as $t_0 = 2r/c$, $w_0$ is the width of the range gate on the time axis, and u is a time shift parameter of the cross-correlation function.

Inserting the equation (2) in the equation (4) yields:

$$C_{k,k+1}(t_0, U) = C_{k,k}(t_0, u-\tau) \qquad (5)$$

The function $C_{k,k}(t_0, u-\tau)$ is an autocorrelation function and, therefore, it is maximum or $u=\tau$. In a hypothetical ideal situation with a uniform axial speed, the maximum of the correlation function corresponds to the time shift T and, consequently, enables determination of the speed of the blood for the echographic excitation of rank k in conformity with the relation:

$$V_z(r,t) = (c/2)(\tau/T) \qquad (6)$$

Referring to FIG. 1, the cross-correlation circuit 302 of the processing system 300 determines the speeds $V_z(r,t)$ by searching the parameter u for which the function $C_{k,k+1}(t_0,u)$ is maximum. To this end, the cross-correlation function is sampled with a sampling step At so as to obtain 2m+1 correlation function values, m being a scalar quantity. The maximum value of these 2m+1 values, corresponding to $u=u_0$, enables measurement of $\tau$ while utilizing the equality:

$$\tau = u_0 \qquad (7)$$

According to this method, no ambiguity exists in the measurement of the speeds because there is only one maximum for this correlation function.

The time shift method derives the real displacement of targets between two successive excitations in time along the same axis Z. Therefore, the range gate must be skillfully chosen. FIG. 3A illustrates a first range gate of dimension $w_0 = 2\ \mu S$ which is applied to a temporal signal $d_k(r,t)$ and FIG. 4B illustrates a second range gate of dimension $w_1 = 4\ \mu S$ which is applied to the later signal $d_{k+1}(r,t)$. FIG. 4C illustrates the correlation C of the two temporal signals $d_k(r,t)$ and $d_{k+1}(r,t)$ which leads to the determination of a correlation peak $C_{MAX}$ for $\tau$ of the order of $0.3\ \mu S$, enabling calculation of the speed $V_z(r,t)$ by way of the relation (6).

Figure 4:
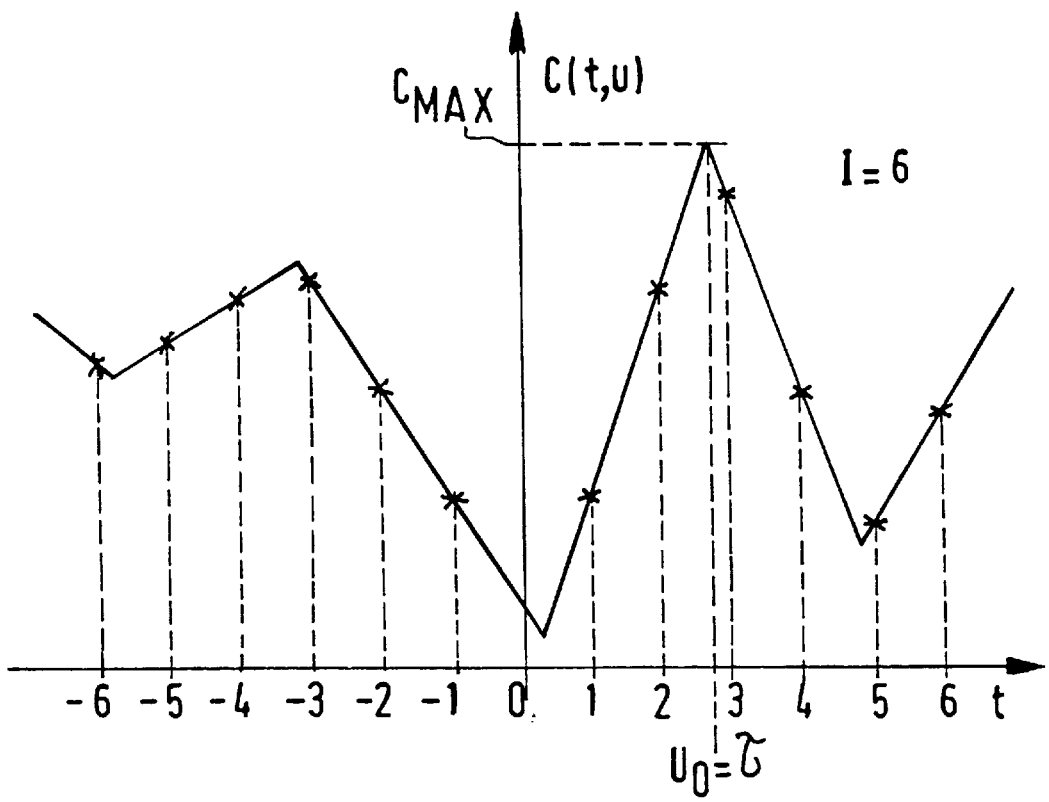
FIG. 4 illustrates a 1-bit correlation signal.

In order to eliminate the errors which are inherent of the sampling during the determination of the maximum of the correlation function, the processing system 300 advantageously includes a multiplexing-interpolation circuit 303 which, on the basis of the values of correlation functions, provides a more exact estimate of the value of the correlation peak and hence of the corresponding speed. According to this type of processing, the correlation between signals is a so-called 1-bit correlation in a sense that the previously used signals $y_{k+1}(r,t)$ and $y_k(r,t)$ are reduced to their sign. It is known that in that case the peak $C_{MAX}$ of the correlation function is shaped as an isosceles triangle. As is shown in FIG. 4, knowledge of this shape enables the correlation calculation to be performed exclusively in discrete points of the temporal signals and, once a given number of points has been determined, on the basis of the highest point and its two neighbors a complete reconstruction of the correlation peak $c_{MAX}$ can be performed by linear interpolation, enabling accurate determination of the location of $u_0 = \tau$ wherefrom $V_z(r,t)$ can be deduced.

Figure 5:
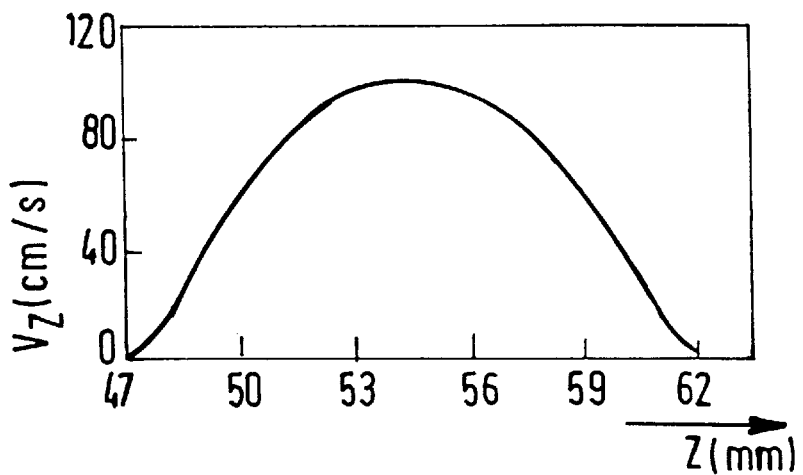
FIG. 5 illustrates a speed profile along an echographic excitation axis Z.

Referring to FIG. 1, the values found for the speed V(t,z) are stored in a memory 304 for storage for the purpose of later operations. As is shown in FIG. 5, plotting the speed values $V_z(r,t)$ in cm/s on the ordinate and the depths r in mm on the abscissa yields a profile of the speeds along the axis Z in the artery at the instant t. Moreover, since the axis Z is discretized in N points to one side of 0 and in N points to the other side of 0, the speed profile is discretized with the same number of points.

Referring to FIG. 1, by using known visualization means a color image of the blood flow, derived from the evolution in time of the speed profile in the vessel, can be displayed on a screen 305. The color encoding of the speed in this image is called CVI (Color Velocity Imaging).

An important advantage of the 1-bit correlation echographic method consists in that the speed profiles are acquired in real time. However, any other method capable of supplying data concerning the speed of the blood in a vessel with a sufficiently high precision can be used for successfully carrying out the evaluation of the viscosity and the pressure gradient as described hereinafter.

The speed profiles of the blood in the same location Z vary in time. The characteristics of a fluid, such as the viscosity, the compressibility, the isotropy; the nature of the flow, such as a laminar or turbulent nature; the properties of the tube containing the fluid, such as the rigidity, the elasticity or the visco-elasticity; and the shape of the pressure gradient, such as wide-band or narrow-band, are parameters which govern the shape of the speed profiles.

It is assumed hereinafter that the blood in an artery is similar to a Newtonian fluid which has a laminar flux and flows in a rigid tube. As is illustrated in FIG. 5, for a pressure gradient dP/dx the speed V(r,t) satisfies a Navier-Stokes rule which is expressed by the known formule (8):

$$-\frac{dP}{dx} = \rho\left(\frac{dV}{dt}\right) - \mu\left(\frac{d^2V}{dr^2}\right) + \frac{1}{r}\frac{dV}{dr} \qquad (8)$$

in which $\rho$ is the density of the fluid and p is the viscosity.

The Navier-Stokes rule, linking the viscosity and the pressure gradient to the speed, however, does not enable direct calculation of the viscosity of the fluid and the pressure gradient as a function of the speed of the fluid. The calculation of the viscosity of the fluid by inversion of the Navier-Stokes equation gives rise to complex analytical expressions.

According to the invention these difficulties are avoided and the viscosity and the pressure gradient are determined in real time by means of a data processing procedure which includes an inversion of the relation (8) which consists in estimating the viscosity and the pressure gradient on the basis of the data supplied by speed profiles which have preferably been determined in advance as described above.

Assuming a laminar flow, the Navier-Stokes equation governs the variations of the speed V(r,t) for r and t given. For the discrete points $R_J$ from $R_0$ to $R_N$, having the spatial co-ordinates $r_J$ from $r_0$ to $r_N$ on the axis Z, the integration of the Navier-Stokes equation (8) between $r=r_1$ and $r=r_J$ yields the following expression (9), the radial derivative of $V_X$ being zero:

$$\frac{\rho}{\pi r_j} \frac{dQ(r_j)}{dt} = -\frac{\partial P}{\partial x} - \mu \frac{2}{R} \frac{\partial V_X(r_j)}{\partial r} \tag{9}$$

in which $r_j$ is the scanning depth.

Each member of the equation (10) is a function of the time t and of the radius $r_j$. For each time sample the relation may be written in vectorial form, each vector being formed by the values of different quantities at different scanning depths $r_j$. Thus:

$$y = \begin{bmatrix} \frac{\rho}{\pi r_1^2} \frac{dQ(r_1)}{dt} \\ \frac{\rho}{\pi r_N^2} \frac{dQ(r_n)}{dt} \end{bmatrix}; \quad h = \begin{bmatrix} \frac{2}{r_1} \frac{dV_X}{dr}(r_1) \\ \frac{2}{r_n} \frac{dV_X}{dr}(r_n) \end{bmatrix}; \tag{10}$$

$$\delta = \delta \begin{bmatrix} 1 \\ 1 \\ 1 \end{bmatrix} = -\frac{\partial P}{\partial x} \begin{bmatrix} 1 \\ 1 \\ 1 \end{bmatrix}$$

The equation of the direct problem can thus be written as:

$$y = \mu h + \delta + b \tag{11}$$

where b is Gaussian white noise which models the measuring errors. In conformity to the equation (11), y is a Gaussian vector whose mean value equals:

$$\mu h + \delta \tag{12}$$

The essential phase of the method consists in inverting this equation which models the direct problem (11). The solution to the inverse problem is preferably obtained by means of a known Maximum Likelihood Estimator which is used to estimate the viscosity $\mu$ as well as the pressure gradient $\delta$.

The values $\mu$ and $\delta$ are searched which maximize the likelihood of y, knowing $\mu$ and $\delta$ given by a formula (13):

$$(\hat{\mu}, \hat{\delta}) = \arg\max_{(\mu,\delta)} [p(y|\mu,\delta)] \tag{13}$$

where $p(y|\mu,\delta)$ is the probability of y knowing $\mu, \delta$, and where $\hat{\mu}$ and $\hat{\delta}$ are estimators of $\mu$ and $\delta$ which are called maximum likelihood estimators. This is equivalent to searching of the minimum of a cost function called $W(\mu,\delta)$:

$$w(\mu,\delta) = (y - \mu h - \delta)^T K_n^{-1} (y - \mu h - \delta) \tag{14}$$

where $K_n^{-1}$ is a diagonal matrix whose coefficients are dependent on the reliability assigned to the values of y, yielding the following expressions for $\mu$ and $\delta$:

$$\hat{\mu} = \frac{y^T K_n^{-1} h - \frac{h^T K_n^{-1} 1 y^T K_n^{-1} 1}{1^T K_n^{-1} 1}}{h^T k_n^{-1} h - \frac{h^T K_n^{-1} 1 h^T K_n^{-1} 1}{1^T k_n^{-1} 1}} \tag{16a}$$

$$\hat{\delta} = \frac{h^T K_n^{-1} y - \hat{\mu} h^T K_n^{-1} h}{h^T K_n^{-1} 1} \tag{17a}$$

For a first approximation it is assumed that the noise is identically distributed in such a manner that the matrix $K_n$ is proportional to the identity matrix. This yields a first approximation of the solution:

$$\hat{\mu}(0) = \frac{y^T h - \frac{h^T 1 y^T 1}{1^T 1}}{h^T h - \frac{h^T 1 h^T 1}{1^T 1}} \tag{16b}$$

$$\hat{\delta}(0) = \frac{h^T y - \hat{\mu} h^T h}{h^T 1} \tag{17b}$$

The invention proposes a method of determining the viscosity $\mu$ which is based on this method of resolving the inverse problem, starting with the direct problem formed by the relation (11) and speed profiles preferably determined by means of echography, or by means of any other method yielding equivalent results, while utilizing said maximum likelihood estimator in conformity with the steps described hereinafter.

Figure 6:
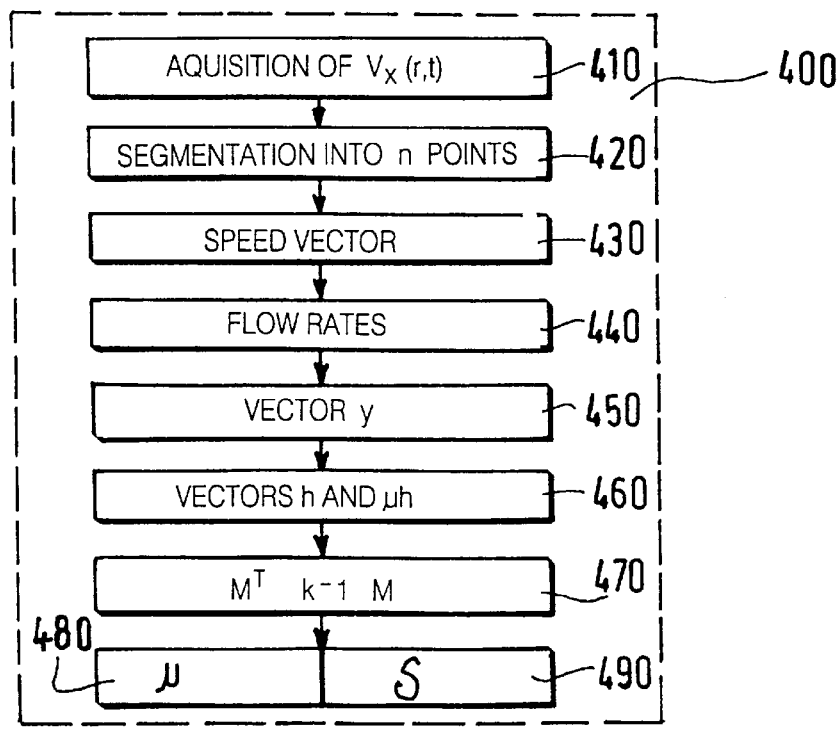
FIG. 6 shows a flow chart in the form of functional blocks illustrating the execution of the method for the transformation of a speed vector in order to produce the values of the viscosity and the pressure gradient in the blood vessel.

Referring to the FIGS. 1 and 6, a processor 400 is associated with the processing system 300 of the echographic apparatus or of a system delivering the speeds. In the case of echography, the processing system 300 is "hardware" in the sense used by those skilled in the art, and the processor 400 is programmed in the equally known software sense. The processor 400 may form part of the echography apparatus or of a workstation coupled to the echography apparatus. The programming of the processor 400 defines the various steps necessary to determine the viscosity $\mu$ and the pressure gradient $\delta$ according to the invention as illustrated by the functional blocks of FIG. 6. This method includes the steps of:

acquisition (410) of speed profiles $V_x(r,t)$ on the basis of speed profiles $V_z(r,t)$ supplied by the processing system 300 while utilizing the formula (1);

sampling (420) of a given discretized speed profile while utilizing a number n of points $R_1$ to $R_n$ from among the N discretization points $R_1$ to $R_N$ in such a manner that $2 \leq n \leq N$; the n segmentation points define radii $r_1$ to $r_n$ of the tube assimilating the blood vessel, generally denoted as $r_j$;

determination (430) of a speed vector which is formed by the speeds at the segmentation points $R_1$ to $R_n$, said speeds being denoted as $V_x(r1)$ to $V_x(r2)$ and in general form as $V_x(ij)$;

evaluation (440) of the flow rates of the liquid in the tube, that is to say of the blood in the vessel, in the sections of the tube which are defined by the radii $r_j$ from $r_1$ to $r_n$, yielding the flow rates $Q(r_j)$ from $Q(r_1)$ to $Q(r_n)$, respectively;

calculation (450) of the vector y in conformity with the formule (10) while performing calculations of the quantities $$\frac{\rho}{\pi r_j} \frac{d Q(r_j)}{d t} \qquad (20)$$

for $r_j$ from $r_1$ to $r_n$;

These calculations (20a) include the sub-steps of:
determination of the flow rate $Q(r_j)$ calculated in conformity with the following equation:

$$Q(rj) = \sum_{i=1}^{i=j} 2\pi r_i V_X(r_i), \qquad (20a)$$

determination of the temporal derivatives of the flow rates $Q(r_j)$ in conformity with:

$$\frac{d Q(r_j)}{d t}, \qquad (20b)$$

for $r_j$ from $r_1$ to $r_n$;
and multiplication of the temporal derivatives of the flow rates by the respective quantities with $r_j$ from $r_1$ to $r_n$;

$$\rho|\pi r_j \qquad (20c)$$

where $\rho$ is the volumic mass of the fluid which is supposed to be approximately equal to 1;

calculation (460) of the vector h in conformity with the equation (10) while performing calculations of the quantities:

$$\frac{2}{r_j} \frac{\partial V_X(r_j)}{\partial r} \qquad (30)$$

being the axial derivatives of the speeds for each point $R_j$ from $R_1$ to $R_N$ defining the radii $r_j$;

calculation (470) of a matrix product:

$$M^T K^{-1} M,$$

where the matrix M is given by the formule:

$$M = y - \mu h - \delta,$$

and where $M^T$ is the transposed matrix of M;

calculation (480) of the viscosity $\mu$ in conformity with the equations (16);
calculation (490) of the pressure gradient $$\delta = -\frac{d p}{d x}$$

in conformity with (17).

In order to carry out the steps 410 to 490, the processor is programmed with the formulas for temporal derivatives of the flow rate, axial derivatives of the speed, and matrix calculation. The processing system 300 automatically supplies the speed profiles in real time and the processor 400 subsequently automatically supplies the viscosity and the pressure gradient with an extremely short overall delay, that is to say in real time.

In order to solve the equation (8) with two unknowns $\mu$ and $\sigma$, in the method according to the invention an inversion of the direct problem thus takes place, utilizing n discretized points of a speed profile in order to solve in reality n equations with two unknowns, where $n \geq 2$. In the case of determination of the viscosity of the blood, it is interesting to select a number of $n>2$ discretization points in order to obtain more than two independent equations with two unknowns for the determination of the 2 unknowns. Actually, if a reduction to $n=2$ is made, occasionally an indetermination may be encountered which does not allow determination of the two unknowns. In these circumstances the calculation means are blocked. Therefore, if a number of $n>2$ segmentation points is advantageously chosen, there will always be a sufficient number of equations for the determination of the two unknowns $\mu$ and $\sigma$.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of determining the viscosity and the pressure gradient of blood flowing in a blood vessel comprising:
   acquiring a plurality of $n \geq 2$ values of speeds of the flowing blood, in correspondence with an equal number of n radii of the blood vessel, determined along a diameter situated in a given axial position, and at different instants,
   forming a vector of the blood speeds from said plurality of values of the blood speeds, and
   evaluating the viscosity and the pressure gradient by transforming said vector of the blood speeds.

2. A method as claimed in claim 1 wherein the step of transforming said vector of the blood speeds further comprises:
   forming a vector of blood flow rates (y) of the blood across sections of the blood vessel which correspond to the n radius values, the vector being formed from the same plurality of $n \geq 2$ values of the blood speeds,
   forming a vector (h) of blood speed derivatives from a quotient of a plurality of $n \geq 2$ radial derivatives of the blood speeds and the corresponding radii, said vector being multiplied by the viscosity ($\mu$) to be determined,
   forming a pressure gradient vector ($\sigma$) from the product of the pressure gradient to be determined and an identity vector,
   forming a direct linear relation which directly links the blood flow rate vector (y) to the blood speed derivative vector (h) multiplied by the viscosity ($\mu$) and to the pressure gradient vector ($\sigma$), and
   evaluating simultaneously the values for the viscosity ($\mu$) and the pressure gradient ($\sigma$) on the basis of said direct linear relation.

3. A method as claimed in claim 2 wherein the step of evaluating simultaneously the values for the viscosity ($\mu$) and the pressure gradient ($\sigma$) further comprises inverting the direct linear relation linking the blood flow rate vector (y) to the blood velocity derivative vector (h) multiplied by the viscosity ($\mu$) and to the pressure gradient vector ($\sigma$).

4. A method as claimed in claim 3 wherein the step of inverting the direct linear relation linking the blood flow rate vector (y) to the blood velocity derivative vector (h) multiplied by the viscosity ($\mu$) and to the pressure gradient vector (σ) further comprises estimating the maximum likelihood of the blood flow rate vector (y) while knowing the viscosity (μ) and the pressure gradient (σ).

5. A method as claimed in claim 4 wherein the step for estimating the maximum likelihood of the blood flow rate vector (y) while knowing the viscosity (μ) and the pressure gradient (σ) further comprises:

evaluating, on the basis of said direct linear relation, a first matrix (M such that: M=y−μh−σ) equal to the blood flow rate vector minus the viscosity times the blood velocity derivative vector minus the pressure gradient vector, and a second matrix ($M^T$) which is the transpose first matrix, evaluating a third matrix (K) which is a diagonal matrix whose coefficients are dependent on a noise distribution, and performing a search for the minimum of a cost function (W) which is the product of the first, the third and the second matrix ($MK^{-1}M^T$) or estimating said maximum likelihood of the blood flow rate vector (y) while knowing the viscosity (μ) and the pressure gradient (σ).

6. A method as claimed in claim 5 wherein the third diagonal matrix (K) is proportional to the identity matrix, the noise distribution being considered to be uniform.

7. A method as claimed in claim 2 wherein the number of blood speed values is two (n=2), and wherein the the step of evaluating simultaneously the viscosity (μ) and pressure gradient (σ) values further comprises:

forming a pair of direct linear relations linking the blood flow rate vector (y) to the blood speed derivative vector (h) multiplied by the viscosity (μ) and to the pressure gradient (σ), wherein the direct linear relations have the form of the blood flow rate vector being equal to the viscosity times the blood speed derivative vector minus the pressure gradient vector, and solving the pair of direct linear relations using the two blood flow rate values and the two blood speed derivative values in order to provide the viscosity (μ) and the pressure gradient (σ).

8. A method as claimed in claim 1 wherein the step of acquiring a plurality of blood speed values further comprises:

acquiring temporal signals supplied by an ultrasonic transducer scanning a blood vessel along an echographic excitation axis (Z), processing the temporal signals in the temporal domain in order to supply temporally correlated signals and a blood speed profile discretized in the direction of the excitation axis, and selecting a number of n≧2 blood speed values from the blood speed profile at different scanning depths (r) on the excitation axis (Z) in the blood vessel for acquiring a plurality of blood speed values.

9. A method as claimed in claim 8 wherein the step of processing the temporal echographic signals further comprises performing a 1-bit temporal correlation.

10. The method of claim 2 wherein the step of acquiring the blood speed values further comprises:

acquiring temporal signals supplied by an ultrasonic transducer scanning a blood vessel along an echographic excitation axis (Z), processing the temporal signals in the temporal domain in order to supply temporally correlated signals and a blood speed profile discretized in the direction of the excitation axis, and selecting a number of n≧2 blood speed values from the blood speed profile at different scanning depths (r) on the excitation axis (Z) in the blood vessel for acquiring a plurality of blood speed values.

11. An echography apparatus for the measurement and display of physiological parameters of blood flowing in a blood vessel comprising:

means for acquiring temporal signals supplied by an ultrasonic transducer scanning a blood vessel along an echographic excitation axis (Z), means for processing the temporal signals in the temporal domain in order to supply temporally correlated signals and a blood speed profile discretized in the direction of the excitation axis (Z), and means for estimating a blood speed vector on the basis of a number of n≧2 speed values selected on the speed profile at different scanning depths (r) on the excitation axis (Z) in the blood vessel, and means for evaluating the viscosity of the blood (μ) and the pressure gradient (σ) by transformation of said speed vector by utilizing a method as claimed in claim 2.

* * * * *